(12) United States Patent
Sarama et al.

(10) Patent No.: US 10,005,670 B2
(45) Date of Patent: Jun. 26, 2018

(54) CALCIUM POLYPHOSPHATE SALT PARTICLES AND METHOD OF MAKING

(71) Applicant: Sunny Delight Beverages Co., Cincinnati, OH (US)

(72) Inventors: Robert J. Sarama, Loveland, OH (US); Gregory Arcuino, Cincinnati, OH (US)

(73) Assignee: Sunny Delight Beverages Co., Cincinnati, OH (US)

( * ) Notice: Subject to any disclaimer, the term of this patent is extended or adjusted under 35 U.S.C. 154(b) by 201 days.

(21) Appl. No.: 15/066,678

(22) Filed: Mar. 10, 2016

(65) Prior Publication Data

US 2016/0325997 A1    Nov. 10, 2016

Related U.S. Application Data

(60) Provisional application No. 62/157,680, filed on May 6, 2015.

(51) Int. Cl.
| | |
|---|---|
| *C01B 25/40* | (2006.01) |
| *C01B 25/44* | (2006.01) |
| *C01B 25/38* | (2006.01) |
| *C01B 25/45* | (2006.01) |
| *A23L 2/44* | (2006.01) |
| *C01B 25/32* | (2006.01) |
| *A61K 33/42* | (2006.01) |
| *A23L 2/52* | (2006.01) |
| *A23L 33/16* | (2016.01) |

(52) U.S. Cl.
CPC ............... *C01B 25/32* (2013.01); *A23L 2/44* (2013.01); *A23L 2/52* (2013.01); *A23L 33/16* (2016.08); *A61K 33/42* (2013.01); *C01B 25/40* (2013.01); *A23V 2002/00* (2013.01); *C01B 25/385* (2013.01); *C01B 25/44* (2013.01); *C01B 25/45* (2013.01)

(58) Field of Classification Search
None
See application file for complete search history.

(56) References Cited

U.S. PATENT DOCUMENTS

| | | | | |
|---|---|---|---|---|
| 2,852,341 | A * | 9/1958 | Bell | C01B 25/40 423/267 |
| 4,010,241 | A * | 3/1977 | Mosse | C01B 7/191 423/304 |
| 4,360,625 | A * | 11/1982 | Griffith | C01B 25/44 423/306 |
| 4,696,826 | A | 9/1987 | Leusner et al. | |
| 4,906,482 | A | 3/1990 | Zemel et al. | |
| 5,431,940 | A * | 7/1995 | Calderas | A23F 3/163 426/271 |
| 6,126,980 | A * | 10/2000 | Smith | A23L 2/44 426/330.3 |
| 6,261,619 | B1 * | 7/2001 | Calderas | A23F 3/163 426/271 |
| 6,268,003 | B1 * | 7/2001 | Calderas | A23F 3/163 426/271 |
| 6,294,214 | B1 * | 9/2001 | Calderas | A23F 3/163 426/330.3 |
| 7,094,282 | B2 | 8/2006 | Lin et al. | |
| 7,494,614 | B2 * | 2/2009 | Pilliar | A61L 15/24 264/666 |
| 2009/0291821 | A1 * | 11/2009 | Gard | A23B 4/24 501/32 |
| 2013/0143737 | A1 * | 6/2013 | Varadachari | C05B 13/06 504/101 |
| 2014/0162364 | A1 * | 6/2014 | Anitua Aldecoa | C04B 38/0064 435/395 |
| 2014/0199439 | A1 | 7/2014 | Sarama et al. | |
| 2016/0324893 | A1 | 11/2016 | Arcuino et al. | |

FOREIGN PATENT DOCUMENTS

| | | |
|---|---|---|
| GB | 2 532 283 A | 5/2016 |
| WO | WO 00/53036 A1 | 9/2000 |
| WO | WO 01/72144 | 10/2001 |
| WO | WO 2014/160920 A1 | 2/2014 |

OTHER PUBLICATIONS

International Search Report and Written Opinion dated Mar. 15, 2016 for Application No. PCT/US2016/022451, 16 pgs.
International Search Report and Written Opinion dated May 31, 2016 for Application No. PCT/US2016/022460, 15 pgs.
U.S. Appl. No. 15/066,652, filed Mar. 10, 2016.
Wilson, Pamela. The Good on Cooking Oils. Downloaded Dec. 26, 2016, from http://www.abc.net.au/health/thepulse/stories/2012/04/24/3471676.htm.
CRC Handbook of Food Additives, Second edition. vol. 1. Edited by Thomas Furia. 1972. CRC Press, Boca Raton Florida. pp. 628-629.
Excerpt from Wikipedia entry for soy milk. From: Wikipedia entry for Soy Milk, downloaded Dec. 21, 2016 from https://en.wikipedia.org/wiki/Soy_milk.

* cited by examiner

*Primary Examiner* — Wayne Langel
(74) *Attorney, Agent, or Firm* — Frost Brown Todd, LLC

(57) ABSTRACT

An equilibrium solution, such as a beverage product, containing a calcium salt of a sequestrant (such as calcium hexametaphosphate), coordinated compound of a calcium sequestrant and a sequestrant allows the delivery of bioavailable calcium while maintaining the preservative qualities of the sequestrant (such as sodium hexametaphosphate). In one embodiment, the reaction of a salt such as calcium hydroxide and a sequestrant such as sodium potassium hexametaphosphate (sodium potassium polyphosphate) yields such an equilibrium solution in a beverage matrix. Calcium hexametaphosphate having a relatively short phosphate chain is disclosed, as well as the method of making that material, and beverage compositions containing the material together with a sequestrant preservative, such as SHMP.

12 Claims, No Drawings

CALCIUM POLYPHOSPHATE SALT PARTICLES AND METHOD OF MAKING

The present application is based on and claims priority from U.S. Provisional Patent Application Ser. No. 62/157,680, Sarama and Arcuino, filed May 6, 2015, incorporated herein by reference.

BACKGROUND

The present invention relates to the formulation of mineral fortified beverage products containing sodium hexametaphosphate as a preservative.

Beverage products frequently utilize sodium hexametaphosphate (SHMP) as a preservative. It is important to have an effective preservative in beverage products since such products tend to require a relatively long shelf life from manufacture to retail outlet to drinking by the consumer. SHMP, although often referred to as a hexametaphosphate, technically is a polyphosphate and a powerful chelating agent. The SHMP functions as a preservative by extracting divalent metallic ions from microbial enzymatic systems. This prevents calcium, iron and magnesium utilization by microorganisms; this interrupts their physiology, resulting in the organisms' death.

While it is desirable to provide vitamin or mineral fortification in some beverage products, particularly beverage products aimed at children, such supplementation can present formulation difficulties in beverages with chelating preservatives. For example, if a beverage product is to be fortified with vitamin D3, federal regulations require that the beverage also be fortified with calcium. Calcium, however, can deactivate the SHMP preservative, thereby significantly decreasing the shelf-life of the product. Thus, the beverage must be formulated such that the calcium does not deactivate the SHMP or otherwise impede its function, the calcium must also be bio-available, not produce unacceptable tastes or colors, must not settle out of the product, must be able to be processed on a large scale, and not add significant cost to the beverage product. Thus, the goal in formulating beverages, and particularly the goal in the present invention, is to develop a form of calcium which is an effective dietary supplement (i.e., bio-available), but which does not deactivate the SHMP preservative, and which is safe, cost-effective and easy to use in a beverage product. In addition, the calcium material utilized in the beverage cannot impart off-flavors or bad mouthfeel to the product and must be easy to incorporate within the product. That is what the present invention accomplishes.

Specifically, SHMP is a powerful chelating agent. It functions as a preservative by extraction of divalent metallic ions (e.g., calcium, iron, magnesium) from microbial enzymatic systems. The extracted metals are no longer available to the microbes and so the microbes enter a stationary phase and, finally, a death phase.

It has been estimated to require 0.24 g of a polyphosphate (e.g., SHMP) to kill $1\times10^3$ CFU's (colony-forming units) of microorganisms. The level of calcium contained in $1\times10^3$ CFU's of microorganisms is estimated to be approximately $2.6\times10^{-8}$ g. The addition of 100 mg of calcium to a beverage containing SHMP will inactivate the SHMP and support the growth of $3.85\times10^9$ CFU's.

The question arises as to how best to add calcium to a beverage containing SHMP as required by 21 CFR 172.380, in order to supplement with Vitamin D. In addition, the calcium must not deactivate the SHMP or impede its function, the calcium must be bio-available, produce no unacceptable taste or color, must not precipitate out and be able to be processed on a large scale.

The present invention provides a calcium polyphosphate product (e.g., calcium hexametaphosphate) which can be used to provide a bio-available source of calcium to a beverage product without deactivating the SHMP preservative in that beverage product. The present application also describes the formation of calcium hexametaphosphate particles, particularly coated particles, and also describes methods of making the calcium polyphosphate-calcium hexametaphosphate material. Finally, the present invention teaches how to formulate the calcium polyphosphate so as to minimize any off-tastes.

BRIEF SUMMARY

It has been discovered that a calcium polyphosphate salt can be produced and maintained in equilibrium with SHMP in such a manner so as to not affect the preservative action of SHMP. The average polyphosphate chain length of SHMP is 19-25, which makes it a very strong chelating agent. It has been found that by producing a calcium polyphosphate salt with a phosphorus chain length of 11-15, the salt not only remains in equilibrium with SHMP, but releases its calcium cations at gastric pH making the calcium bio-available.

The ratio of calcium to lower chain polyphosphate is critical as well. The optimum molar ratio of calcium polyphosphate is about 4:1. Lowering the level causes overuse of polyphosphate whereas exceeding a ratio of about 4:1 causes the formation of a sticky amorphous glass structure which physically separates from the aqueous base during preparation. This amorphous glass solid is unstable in that form and will not mix homogenously with aqueous beverages.

The present application therefore describes a calcium polyphosphate salt, such as a calcium hexametaphosphate salt, in soluble form, which has a calcium/polyphosphate molar ratio of from about 2.5:1 to about 4.5:1, and wherein the polyphosphate has a phosphorus chain length of from about 9 to about 16, for example, from about 11 to about 15.

The present application also describes a method of making a calcium polyphosphate salt, in particulate form, comprising the steps of:
   (a) preparing a calcium phosphate salt having a phosphorus chain length of from about 9 to about 16, and a calcium:polyphosphate molar ratio of from about 5:1 to about 9:1 (especially about 5.5:1), in the form of an amorphous glass solid;
   (b) dehydrating the amorphous glass solid to form a solid having a water content no greater than about 0.1%; and
   (c) processing the solid (such as by grinding) to form particles having an average particle size no greater than about 0.5 μm.

The present application also describes two methods for the preparation of the calcium polyphosphate salt; this can be done in situ thereby allowing the completed reaction mixture to be made directly into a beverage product. The first such method which directly reacts calcium with the polyphosphate includes the following steps:
   (a) directly reacting a metallic polyphosphate (such as a sodium potassium polyphosphate) having a phosphorus chain length of from about 9 to about 16 (such as from about 11 to about 15), with a calcium source selected from calcium hydroxide, calcium oxide, calcium phosphate, calcium carbonate, calcium glycerophosphate, calcium pyrophosphate, calcium metaphosphate or any other calcium source ionizable at aqueous, acidic solution, and mixtures thereof, in an aqueous near neutral (pH=about 6 to about 7.5) medium, the molar ratio of polyphosphate to calcium source being from about 2.5:1 to about 4.5:1; and (b) adding a minor portion, for example about 25% of the total added, the total being from about 0.18 wt % to about 0.725 wt %, of an organic or mineral acid toward the end of this reaction to complete the dissociation of the calcium from its counter moiety and complete the transfer of calcium to the polyphosphate substrate thereby forming the soluble calcium phosphate salt.

The solubility of the calcium source will typically be low in near neutral pH aqueous medium and so will slowly react with the polyphosphate, for example, having a 10-15 minute reaction time.

That completed reaction mixture can then be used to formulate a beverage in situ by the addition of water, sodium hexametaphosphate, flavor, color and sweetener (and, if desired, other conventional beverage components).

The second such method for preparing the calcium polyphosphate salt comprises the steps of:

(a) preparing an aqueous solution of an organic mineral acid (such as citric acid), together with from about 1.3 parts to about 10 parts of a calcium source selected from calcium hydroxide, calcium oxide, calcium phosphate, calcium chloride, calcium glycerophosphate, calcium pyrophosphate, calcium metaphosphate, or any calcium source ionizable at aqueous, acidic solution, and mixtures thereof, to one part polyphosphate, said solution having a pH of from about 1.5 to about 3.5, with the amount of calcium used based on a calcium polyphosphate molar ratio from about 2.5:1 to about 4.5:1;

(b) forming a separate aqueous solution of a metallic (such as a sodium or sodium/potassium) polyphosphate having a chain length of from about 9 to about 16 (such as from about 11 to about 15), at such a concentration as to form a calcium polyphosphate soluble salt with a molar ratio from about 2.5:1 to about 4.5:1; and (c) with agitation, adding the calcium and surrogate solution (step (a)) to the polyphosphate solution (step (b)), thereby forming the calcium polyphosphate salt.

This completed reaction mixture can be used to formulate a beverage in situ by addition of water, sodium hexametaphosphate, flavor, color and sweetener (and, if desired, other conventional beverage components).

The calcium polyphosphate particles herein are insoluble in a beverage product of typical pH, such as between pH 2.8 and 7.6. The formation of the particles lends itself to a purification step that allows the removal of byproducts that may impact flavor (i.e., potassium ions). This higher calcium loaded polyphosphate material does not affect the preservative action of SHMP and releases its calcium cations at gastric pH, making the calcium bioavailable.

It has also been discovered that an oil-in-water (O/W) emulsion, such as those used to provide beverage opacity or disperse flavors, can mask the unpleasant flavor that may come from displaced ions (e.g., potassium) that are present as a result of the making of the calcium polyphosphate.

Further, it has been found that, in addition to the flavor masking of the O/W emulsion, sodium ions must also be present with the emulsion to optimally mask the unpleasant flavor that may come from displaced ions (e.g., potassium) that are present as a result of the making of the calcium polyphosphate.

The present invention thus provides a calcium polyphosphate product (e.g., calcium metaphosphate or calcium polyphosphate) which:

(a) is soluble and does not deactivate a chelating preservative, such as SHMP, and can be used to provide a bio-available source of calcium to a beverage product;

(b) is in particulate form, free from extraneous matter that may impact flavor (e.g., potassium ions), does not deactivate a chelating preservative, such as SHMP, and can be used to provide a bio-available source of calcium to a beverage product;

(c) can be used in combination with an oil-in-water emulsion that masks the unpleasant flavor that may be associated with potassium ions that are present as a result of the making of the calcium polyphosphate; and (d) utilizes sodium ions in addition to the oil-in-water emulsion that masks the unpleasant flavor that may be associated with potassium ions that are present as a result of the making of the calcium polyphosphate.

All references herein to polyphosphates are interchangeable with the terms hexametaphosphates and metaphosphates, including reference to their cyclic or linear forms, and can refer to any member of their metallic salts. All percentages and ratios stated herein are "by weight", unless otherwise specified. Further, all patents, patent applications and other publications cited in this application are incorporated by reference herein.

DETAILED DESCRIPTION

The present invention relates to calcium polyphosphate materials (such as calcium hexametaphosphate), containing relatively short polyphosphate chain lengths and utilizing specific calcium:phosphate molar ratios. These materials can be used to provide calcium supplementation to beverages, particularly beverages which use a chelating preservative (such as SHMP) without deactivating that preservative. The methods of making these materials are also disclosed in this application.

It has been discovered that a calcium polyphosphate salt can be produced and maintained in equilibrium with SHMP in a beverage product in such a manner as to not affect the preservative activity of the SHMP in that beverage. The average polyphosphate chain length of SHMP is from 19 to 25. This makes for a very strong chelating agent (which accounts for SHMP's excellent preservative characteristics). It has now been found that by producing a calcium polyphosphate salt with a relatively short phosphorus chain length of from about 9 to about 16, such as from about 11 to about 15, the calcium polyphosphate not only remains in equilibrium with SHMP (i.e., does not ruin SHMP's preservative properties) but also releases its calcium cation at gastric pH making the calcium bio-available.

The ratio of calcium to lower chain polyphosphate in the composition is important. The molar ratio of calcium to polyphosphate in the material is from about 2.5:1 to about 4.5:1, such as about 4:1. Lowering the ratio causes the overuse of polyphosphate, whereas significantly exceeding the ratio causes the formation of a sticky, amorphous, glass structure which physically separates from the aqueous base during preparation.

This amorphous glass solid is unusable in that form to be a calcium supplement in a beverage, and will not itself mix homogeneously with aqueous beverages. However, it has been found that this amorphous glass solid can be dehydrated, ground or physically processed by a jet mill or similar methods to produce small particles. These particles can then be added back to the SHMP-containing beverage with great success. The amorphous glass solid can be decanted and dehydrated by filtering, evaporation, solvent extraction, microwave heating or other similar means, for example, such that it has a water content of no greater than about 0.1%, preferably no greater than about 0.05%. The particles formed by grinding this solid typically have an average particle size of no greater than about 0.5 µm, such as from about 0.1 µm to about 0.3 µm. This small particle size is primarily important to avoid product grittiness or otherwise inappropriate mouthfeel for the consumer. By producing calcium phosphate amorphous glass solid at a molar ratio of from about 5:1 to about 9:1, such as about 5.5:1, calcium:short chain polyphosphate, a high calcium loaded salt, suitable for use after dehydration and particle processing is produced. An added benefit of this approach is that any metallic ions (sodium, potassium, etc.) originating from the starting shorter chain polyphosphate are essentially removed during the isolation of the amorphous glass solid.

The selection of shorter chain polyphosphate materials ideally has a phosphorus chain length of from about 9 to about 16, such as from about 11 to about 15, but longer chain lengths, for example 19-25, can be used particularly in conjunction with shorter chain length polyphosphates. They can, for example, be selected from the group consisting of metal salts of polyphosphates and metaphosphates, such as sodium metaphosphate, sodium calcium metaphosphate, sodium calcium polyphosphates, or sodium potassium metaphosphate, as well as other salts of metaphosphates or polyphosphates either of mono, binary, tertiary salts (e.g., a sodium potassium magnesium polyphosphate) encompassing all ratios of salt, for example, a sodium potassium polyphosphate with a sodium:potassium molar ratio of from about 1:9 to about 9:1.

The calcium polyphosphate salts defined herein can be synthesized in several ways. The first is to directly react the metallic short chain polyphosphate with a calcium source (for example, calcium hydroxide) in an aqueous neutral medium. Since the solubility of calcium hydroxide is very low in an aqueous medium, the calcium hydroxide solely reacts over the course of from about 5 to about 20 minutes, such as from about 10 to about 15 minutes, as calcium is transferred from the calcium hydroxide to the polyphosphate. A small amount of organic or mineral acid, such as citric acid, is added toward the end of this process to complete the dissociation of calcium from its hydroxide moiety and complete the transfer of calcium to the polyphosphate substrate.

Specifically, in this first method of making the calcium polyphosphate salt, where there is a direct reaction of the calcium with the polyphosphate, the following steps are utilized:
  (a) reacting a metallic polyphosphate having a phosphorus chain length of from about 9 to about to about 16, with a calcium source selected from calcium hydroxide, calcium oxide, calcium phosphate, calcium chloride, calcium carbonate, calcium glycerophosphate, calcium pyrophosphate, calcium metaphosphate, or any calcium salt ionizable at aqueous, acidic solution, and mixtures thereof, in an aqueous medium, having a pH of from about 6 to about 7.5, the molar ratio of calcium to polyphosphate source being from about 2.5:1 to about 4.5:1;
  (b) adding to the reaction mixture from about 0.18 wt % to about 0.725 wt % of an organic or mineral acid (such as citric acid, malic acid, tartaric acid, phosphoric acid, carbonic acid, lactic acid, gluconic acid, acetic acid, and mixtures thereof), thereby forming the calcium phosphate salt.

In a second method of preparing the soluble calcium polyphosphate salt described herein, an organic acid is utilized as a surrogate carrier of the calcium. This is accomplished by first preparing an aqueous solution of the acid (for example, citric acid). To this aqueous solution the correct amount of calcium salt (e.g., calcium hydroxide) is added. The amount of calcium salt used is based on the desired ratio of calcium to metaphosphate or polyphosphate. Because the solution is acidic (pH of from about 1.5 to about 2.5), calcium hydroxide immediately dissociates allowing the calcium to react with the acid forming a salt (e.g., calcium citrate). Separately, the polyphosphate is solubilized in water. This polyphosphate is reacted with the calcium salt (i.e., the surrogate carrier solution) (e.g., calcium citrate, calcium malate, calcium tartrate, calcium phosphate, calcium lactate, calcium acetate, calcium chloride, calcium carbonate, calcium gluconate, and mixtures thereof) by mixing of the calcium salt solution into the polyphosphate solution. The calcium is then quickly chelated or transferred from the calcium salt to the polyphosphate resulting in the formation of calcium polyphosphate.

More specifically, in the second method of preparing the calcium polyphosphate salt, where there is a surrogate carrier of the calcium, the following steps are utilized:
  (a) preparing an aqueous solution of an organic or mineral acid (such as citric acid, malic acid, tartaric acid, phosphoric acid, carbonic acid, lactic acid, gluconic acid, acetic acid, hydrochloric acid, and mixtures thereof) together with a calcium source selected from calcium hydroxide, calcium oxide, calcium phosphate, calcium chloride, calcium carbonate, calcium glycerophosphate, calcium pyrophosphate, calcium metaphosphate, or any calcium source ionizable at aqueous, acidic solution, and mixtures thereof, to achieve a calcium to polyphosphate molar ratio of from about 2.5:1 to about 4.5:1 when mixed with the polyphosphate solution, said solution having a pH of from about 1.5 to about 3.5, such as from about 1.5 to about 2.5;
  (b) forming a separate aqueous solution of from about 3 wt % to about 5 wt % of metallic polyphosphate having a phosphate chain length of from about 9 to about 16, such as from about 11 to about 15; and
  (c) mixing the calcium salt solution into the polyphosphate solution thereby forming the calcium polyphosphate salt.

The metallic polyphosphate utilized in this reaction can, for example, be a sodium or a sodium/potassium polyphosphate. For health reasons, it is desirable to keep sodium levels relatively low; thus, the Na/K mixture can preferably include from about 50% to about 75% potassium. Examples of the calcium polyphosphate formed by the reaction include calcium metaphosphate, calcium sodium metaphosphate, calcium sodium potassium metaphosphate, calcium sodium polyphosphate, and calcium sodium potassium polyphosphate. The above reaction can be optimized to form a material which includes a relatively high loading of calcium so that fewer particles can be used in the beverage product to attain the desired level of calcium in that product; this will minimize aesthetic concerns in the final beverage product.

Once the reaction is completed, the calcium polyphosphate particles can be separated out and incorporated into a separate beverage making process. In the alternative, the beverage can actually be formed in situ in the reaction mixture used to prepare the calcium polyphosphate material. In order to achieve that in situ beverage formulation, water, preservative (such as sodium hexametaphosphate), flavor materials, colorants, and sweeteners (as well as other formulation materials well-known in the beverage art) are added to the reaction mixture. All of these materials are well-known to those skilled in the beverage art and they are used at their conventional levels for their conventional purposes. The finished beverage compositions typically contain from about 100 mg to about 300 mg of calcium per serving, and from about 0.1 wt % to about 0.18 wt % of the SHMP preservative.

The calcium source utilized in these reactions is selected to be compatible with a beverage product. As an example, calcium hydroxide or calcium oxide can be used because water is then formed in the reaction. Calcium phosphate can be used, but care must be taken to be sure that the phosphorus RDI is not exceeded in the final product. The reaction needs to drive calcium to the sodium/potassium polyphosphate where it is bound, and not to the acid in the form of calcium citrate because in that instance it would still be available to deactivate the SHMP preservative. Examples of calcium sources which can be used in the present reactions include calcium hydroxide, calcium oxide, calcium phosphate, calcium chloride, calcium carbonate, calcium glycerophosphate, calcium phyrophosphate, calcium metaphosphate, or any calcium source ionizable at aqueous, acidic solution, and mixtures thereof.

The acid selected for use in the reactions defined herein must be edible and have a pKa at low pH so that the acid stays protonated, thereby assuring that the calcium will not bind to it (this is because the calcium acid salt will not prevent the calcium from deactivating the SHMP preservative). Examples of useful acids in the reactions herein include citric acid, malic acid, tartaric acid, phosphoric acid, carbonic acid, lactic acid, gluconic acid, acetic acid, hydrochloric acid, and mixtures thereof.

The reactions defined herein typically take place at a temperature within the range of from about 10 to about 30 degrees C.

In making the particles of the calcium polyphosphate material (i.e., having a high calcium:polyphosphate molar ratio), the amorphous glass solid material is formed, it is allowed to settle and the liquid is decanted off or filtered, and then the remaining amorphous solid material is dried using conventional means, such as a static dryer, solvent extraction, microwave heating or other similar means. This dry material is then ground into calcium polyphosphate particles using conventional means, such as a jet mill, to a particle size which is less than about 0.5 µm, such as from about 0.1 to about 0.3 µm. The particles can be added to the beverage product as is or can be coated (such as with a hydrogenated phospholipid material, for example, lecithin). When used, the particles comprise from about 10 to about 90 weight percent of the calcium polyphosphate material, and from about 90 to about 10 weight percent of the coating material. The coating itself can be carried out using any known coating process, such as using a process by which the coating is sprayed onto the calcium polyphosphate particles and allowed to dry; or by incorporating the particles in a melt of phytosterols and other plant lipids and then spray chilling (prilling) the melt to allow a core of calcium polyphosphate and a coating of phytosterol.

The present application also describes a method of utilizing an oil-in-water (O/W) emulsion, such as those used to provide beverage opacity or disperse flavors, to mask the unpleasant flavor that may come from displaced ions (i.e., potassium) that are present as a result of the making of the soluble calcium phosphate.

Three critical elements support the use of the O/W emulsion as masking agent:

(a) The soluble calcium polyphosphate salt must make contact with the O/W emulsion separately prior to addition of other beverage components; and maximum contact is ensured with the mixture thoroughly agitated, such as with high shear mixing, for a period of contact time of about five minutes or more.

(b) The composition of the O/W emulsion is from about 10% to about 20%, such as about 14%, oil such as food approved oils (e.g., canola oil) used for such purposes; from about 5% to about 10%, preferably about 7%, emulsifier such as modified food starch; from about 68% to about 83%, preferably about 77%, water; and may include necessary preservatives, colors, and flavors to meet desired beverage organoleptics.

(c) The droplet size of the discontinuous phase of the O/W emulsion is less than about 1 µm, such as less than about 0.5 µm; it is preferred that 90% or greater of the droplets are at 0.1 µm; which can be achieved through typical emulsification methods such as high shear mixing or high pressure homogenization. Droplet size can be measured, for example, using a Horiba, Laser Diffraction Particle Size Analyzer.

In addition, the present invention describes utilizing sodium ions in addition to the O/W emulsion to further mask any unpleasant flavor that may come from displaced ions (i.e., potassium) that are present as a result of the making of the soluble calcium phosphate. In formulating such beverages, the sodium concentration is from about 100 ppm to about 500 ppm, such as about 250 ppm, not to exceed about 400 mg per 8 oz serving of the finished beverage; the sodium source is selected from sodium ions present in softened process water, and inorganic or organic salts approved for food use (such as sodium chloride, sodium citrate, sodium malate, sodium tartrate, sodium acetate, encompassing all food approved sodium-containing additives or mixtures thereof).

The following examples are intended to illustrate the present invention and are not intended to be in any way limiting thereof.

Example 1—Direct Method

1. In an appropriate vessel, add 1094 g distilled $H_2O$ (ca. 25% of total water).
2. While high shear mixing the water, add 21.592 g sodium potassium hexametaphosphate (SHMP) to dissolve.
3. While high shear mixing the solution from (2), add 3.831 g $Ca(OH)_2$.
4. Mix for 10-15 minutes.
5. While high shear mixing the solution from (4), add 8.51 g citric acid (ca. 23% of total citric acid).
6. Mix for 5 minutes.
7. In another vessel, add 3280.74 g distilled water (ca. 75% of total water).
8. While high shear mixing the water, add 4.92 g sodium hexametaphosphate (SHMP) to dissolve.
9. While high shear mixing the solution from (8), add 28.71 g citric acid (ca. 78% of total citric acid).
10. To the solution from (9), add flavors, colors and sweeteners and mix well.
11. To achieve the finished beverage, to the solution from (10) add the solution from (6) and mix well.

Example 2—Surrogate Method

1. In an appropriate vessel, add 1094 g distilled $H_2O$ (ca. 25% of total water).

2. While high shear mixing the water, add 21.592 g sodium potassium hexametaphosphate (SKMP) to dissolve.

3. In another vessel, add 1094 g distilled $H_2O$ (ca. 25% of total water).

4. While high shear mixing the solution from (3), add 3.831 g $Ca(OH)_2$.

5. While high shear mixing the solution from (4), add 37.22 g citric acid to dissolve.

6. In another vessel, add 2186.74 g distilled $H_2O$ (ca. 50% of total water).

7. While high shear mixing the water, add 4.92 g sodium hexametaphosphate (SHMP) to dissolve.

8. To the solution from (7) add flavors, colors and sweeteners and mix well.

9. Mix the solution from (5) into the solution from (2).

10. Mix the solution from (9) into the solution from (8) to achieve the finished beverage.

Example 3—Plant Batch

1. Add 80% of the batch's process water to the blend tank and start agitator and recirculation pump.

2. Add the $Ca(OH)_2$ to the tank and agitate to disperse.

3. Add the sodium potassium hexametaphosphate (SKMP) to the above solution as it is being agitated and continue agitating from 5 minutes up to 12 minutes.

4. To the tank add a portion of the citric acid that equals 21.48% of the total citric acid being added to the batch.

5. Mix for 2-5 minutes, then circulate through the recirculation loop to remove any unreacted calcium.

6. While agitating the above solution, add sodium hexametaphosphate (SHMP) to dissolve.

7. Add flavors, colors and sweeteners and agitate to mix ingredients well.

8. Add the remaining citric acid.

9. Add the remaining process water and agitate well until homogenous.

Example 4—Direct Method with Emulsion Flavor Masking

1. In an appropriate vessel, add 1094 g distilled $H_2O$ (ca. 25% of total water).

2. While high shear mixing the water, add 21.592 g sodium potassium hexametaphosphate (SKMP) to dissolve.

3. While high shear mixing the solution from (2), add 3.831 g $Ca(OH)_2$.

4. Mix for 10-15 minutes.

5. While high shear mixing the solution from (4), add 8.51 g citric acid (ca. 23% of total citric acid).

6. Mix for 5 minutes.

7. While high shear mixing the solution from (6) add 25.53 g of oil-in-water emulsion (the o/w emulsion as described herein containing starch, water and canola oil).

8. High shear mix for 10-15 minutes.

9. In another vessel, add 3280.74 g distilled water (ca. 75% of total water).

10. While high shear mixing the water, add 4.92 g sodium hexametaphosphate (SHMP) to dissolve.

11. While high shear mixing the solution from (10), add 28.71 g citric acid (ca. 78% of total citric acid).

12. To the solution from (11), add flavors, colors, and sweeteners and mix well.

13. To achieve the finished beverage, to the solution from (12) add the solution from (8) and mix well.

Example 5—Surrogate Method with Emulsion Flavor Masking

1. In an appropriate vessel add 1094 g distilled $H_2O$ (ca. 25% of total water).

2. While high shear mixing the water, add 21.592 g sodium potassium hexametaphosphate (SKMP) to dissolve.

3. In another vessel add 1094 g distilled $H_2O$ (ca. 25% of total water).

4. While high shear mixing the solution from (3), add 3.81 g $Ca(OH)_2$.

5. While high shear mixing the solution from (4), add 37.22 g citric acid to dissolve.

6. In another vessel, add 2186.74 g distilled $H_2O$ (ca. 50% of total water).

7. While high shear mixing the water, add 4.92 g sodium hexametaphosphate (SHMP) to dissolve.

8. To the solution from (7) add flavors, colors and sweeteners and mix well.

9. Mix the solution from (5) into the solution from (2).

10. While high shear mixing the solution from (9) add 25.53 g of oil-in-water emulsion (the o/w emulsion as described herein containing starch, water and canola oil).

11. High shear mix for 10-15 minutes.

12. Mix the solution from (11) into the solution from (8) to achieve the finished beverage.

Example 6—Plant Batch with Emulsion Flavor Masking

1. Add 80% of the batch's process water to the blend tank and start agitator and recirculation pump.

2. Add the $Ca(OH)_2$ to the tank and disperse.

3. Add the sodium potassium hexametaphosphate (SKMP) to the above solution as it is being agitated and continue agitating from 5 minutes up to 12 minutes.

4. To the tank add a portion of the citric acid that equals 21.48% of the total citric acid being added to the batch.

5. Mix for 2-5 minutes, then circulate through the recirculation loop to remove any unreacted calcium.

6. While high shear mixing the solution from (5) add the oil-in-water emulsion (the o/w emulsion as described herein containing starch, water and canola oil).

7. High shear mix for 10-15 minutes.

8. While agitating the above solution, add sodium hexametaphosphate (SHMP) to dissolve.

9. Add flavors, colors and sweeteners and agitate to mix ingredients well.

10. Add the remaining citric acid.

11. Add the remaining process water and agitate well until homogenous.

Example 7—Direct Method with Emulsion and Sodium Flavor Masking

1. To the process water add sodium citrate to dissolve and bring the water sodium level to 255 ppm, resulting in modified process water (MPW).

2. In an appropriate vessel, add 1094 g MPW (ca. 25% of total water).

3. While high shear mixing the water, add 21.592 g sodium potassium hexametaphosphate (SKMP) to dissolve.

4. While high shear mixing the solution from (3), add 3.831 g $Ca(OH)_2$.

5. Mix for 10-15 minutes.

6. While high shear mixing the solution from (5), add 8.51 g citric acid (ca. 23% of total citric acid).

7. Mix for 5 minutes.

8. While high shear mixing the solution from (7) add 25.53 g of oil-in-water emulsion (the o/w emulsion as described herein containing starch, water and canola oil).

9. High shear mix for 10-15 minutes.

10. In another vessel, add 3280.74 g MPW (ca. 75% of total water).

11. While high shear mixing the water, add 4.92 g sodium hexametaphosphate (SHMP) to dissolve.

12. While high shear mixing the solution from (11), add 28.71 g citric acid (ca. 78% of total citric acid).

13. To the solution from (12), add flavors, colors, and sweeteners and mix well.

14. To achieve the finished beverage, to the solution from (13) add the solution from (9) and mix well.

Example 8—Surrogate Method with Emulsion and Salt Flavor Masking

1. To the process water add sodium citrate to dissolve to bring the water sodium level to 255 ppm, resulting in modified process water (MPW).

2. In an appropriate vessel add 1094 g MPW (ca. 25% of total water).

3. While high shear mixing the water, add 21.592 g sodium potassium hexametaphosphate (SKMP) to dissolve.

4. In another vessel add 1094 g MPW (ca. 25% of total water).

5. While high shear mixing the solution from (4), add 3.81 g $Ca(OH)_2$.

6. While high shear mixing the solution from (5), add 37.22 g citric acid to dissolve.

7. In another vessel, add 2186.74 g MPW (ca. 50% of total water).

8. While high shear mixing the water, add 4.92 g sodium hexametaphosphate (SHMP) to dissolve.

9. To the solution from (8) add flavors, colors and sweeteners and mix well.

10. Mix the solution from (6) into the solution from (3).

11. While high shear mixing the solution from (10) add 25.53 g of oil-in-water emulsion (the o/w emulsion as described herein containing starch, water and canola oil).

12. High shear mix for 10-15 minutes.

13. Mix the solution from (12) into the solution from (9) to achieve the finished beverage.

Example 9—Plant Batch with Emulsion and Salt Flavor Masking

1. Modify the process water to achieve 255 ppm sodium by adding sodium citrate to dissolve.

2. Add 80% of the batch's process water to the blend tank and start agitator and recirculation pump.

3. Add the $Ca(OH)_2$ to the tank and disperse.

4. Add the sodium potassium hexametaphosphate (SKMP) to the above solution as it is being agitated and continue agitating from 5 minutes up to 12 minutes.

5. To the tank add a portion of the citric acid that equals 21.48% of the total citric acid being added to the batch.

6. Mix for 2-5 minutes, then circulate through the recirculation loop to remove any unreacted calcium.

7. While high shear mixing the solution from (6) add the oil-in-water emulsion (the o/w emulsion as described herein containing starch, water and canola oil).

8. High shear mix for 10-15 minutes.

9. While agitating the above solution, add sodium hexametaphosphate (SHMP) to dissolve.

10. Add flavors, colors and sweeteners and agitate to mix ingredients well.

11. Add the remaining citric acid.

12. Add the remaining process water and agitate well until homogenous.

Example 10—Calcium Polyphosphate Particles

1. In an appropriate vessel, add 1094 g distilled $H_2O$ (ca. 25% of total water).

2. While high shear mixing the water, add 21.59 g sodium potassium hexametaphosphate (SKMP) to dissolve.

3. While high shear mixing the solution from (2), add 5.268 g $Ca(OH)_2$.

4. Mix for 5-10 minutes or until mixture begins to clear.

5. Stop agitating.

6. Decant aqueous supernatant containing potassium and sodium ions.

7. Collect amorphous glass precipitate and place into a drying vessel.

8. Dry at 50-58 degrees C. until moisture content is less than 0.1% as measured by Karl Fisher.

9. Pulverize the dried salt and follow with high intensity grinding to achieve appropriate size and distribution as measured by using a Horiba PSA.

10. If particles exceed 0.5 μm, prepare an aqueous slurry using the particles and high shear grind until desired particle size and distribution are achieved.

11. After drying and grinding, the calcium polyphosphate particles can now be utilized in an SHMP-containing beverage where the salt remains insoluble without deactivating SHMP.

What is claimed:

1. A calcium polyphosphate salt having a calcium:polyphosphate molar ratio of from about 5:1 to about 9:1, and wherein the polyphosphate has a phosphorus chain length of from about 9 to about 16, in the form of particles having an average particle size of less than or equal to 0.5 μm.

2. The calcium polyphosphate salt according to claim 1 having an average particle size of from about 0.1 μm to about 0.3 μm.

3. The calcium polyphosphate salt according to claim 2 in the form of particles coated with hydrogenated phospholipid material.

4. The calcium polyphosphate salt according to claim 1 selected from the group consisting of calcium metaphosphate, calcium sodium metaphosphate, calcium sodium potassium metaphosphate, calcium sodium polyphosphate, and calcium sodium potassium polyphosphate.

5. The calcium polyphosphate salt according to claim 4 in the form of calcium sodium potassium polyphosphate or calcium sodium potassium metaphosphate.

6. A method of making calcium polyphosphate salt in particulate form comprising the steps of:
   (a) preparing a calcium phosphate salt having a phosphorus chain length of from about 9 to about 16, and a calcium:polyphosphate molar ratio of from about 5:1 to about 9:1, in the form of an amorphous glass solid;
   (b) dehydrating the amorphous glass solid to form a solid having a water content no greater than about 0.1%; and
   (c) processing the solid to form particles having an average particle size no greater than about 0.5 μm.

7. The method according to claim 6 wherein the calcium polyphosphate salt has a phosphorus chain length of from about 11 to about 15.

8. The method according to claim 7 wherein the calcium polyphosphate salt has a calcium:phosphorus molar ratio of about 5.5.

9. The method according to claim 7 wherein the water content of the dehydrated solid is no greater than about 0.05%.

10. The method according to claim 7 wherein the dehydrated solid is processed by grinding to form particles.

11. The method according to claim 10 wherein the particles have an average particle size of from about 0.1 µm to about 0.3 µm.

12. The method according to claim 7 wherein the calcium polyphosphate salt is selected from the group consisting of calcium metaphosphate, calcium sodium metaphosphate, calcium sodium potassium metaphosphate, calcium sodium polyphosphate, and calcium sodium potassium polyphosphate.

\* \* \* \* \*